United States Patent [19]
Koblish

[11] Patent Number: 6,032,061
[45] Date of Patent: Feb. 29, 2000

[54] CATHETER CARRYING AN ELECTRODE AND METHODS OF ASSEMBLY

[75] Inventor: Josef Koblish, Sunnyvale, Calif.

[73] Assignee: Boston Scientifc Corporation, Natick, Mass.

[21] Appl. No.: 08/803,431

[22] Filed: Feb. 20, 1997

[51] Int. Cl.⁷ ............................. A61N 1/05; A61M 25/00
[52] U.S. Cl. ........................ 600/372; 607/116; 607/119; 600/374
[58] Field of Search ................... 600/372, 374; 607/119, 122, 116

[56] References Cited

U.S. PATENT DOCUMENTS

| | | | |
|---|---|---|---|
| 3,731,376 | 5/1973 | Ackerman | 607/122 |
| 3,769,984 | 11/1973 | Muench | 607/122 |
| 4,444,195 | 4/1984 | Gold . | |
| 4,592,372 | 6/1986 | Beranek . | |
| 5,251,643 | 10/1993 | Osypka | 607/122 |
| 5,354,297 | 10/1994 | Avitall | 606/45 |
| 5,465,716 | 11/1995 | Avitall | 128/642 |
| 5,823,955 | 10/1998 | Kuck et al. . | |
| 5,938,623 | 8/1999 | Quiachon et al. | 600/585 |

FOREIGN PATENT DOCUMENTS

| | | | |
|---|---|---|---|
| 0 580 928 A1 | 7/1992 | European Pat. Off. | A61N 1/05 |
| WO 94/24931 | 11/1994 | WIPO | A61N 5/04 |

Primary Examiner—William E. Kamm
Assistant Examiner—Carl H. Layno
Attorney, Agent, or Firm—Lyon & Lyon LLP

[57] ABSTRACT

An electrophysiology catheter which includes: a catheter tube having a band of electrically conductive material extending around substantially the entire circumference of the catheter tube, the conductive material being non-adhesive; a flexible electrical conductor within the catheter tube, the electrical conductor having a free end extending through an opening in the catheter tube, the free end lying along and being in contact with a portion of the band of non-adhesive and being in electrical contact with the band of non-adhesive electrically conductive material; and an electrically conductive electrode positioned over and in electrical contact with the band of non-adhesive electrically conductive material and the free end of the conductive wire, the electrode being substantially cylindrical and having a distal end and a proximal end.

10 Claims, 2 Drawing Sheets

CATHETER CARRYING AN ELECTRODE AND METHODS OF ASSEMBLY

FIELD OF THE INVENTION

The invention relates to catheters carrying an electrode or plurality of electrodes and methods for assembling catheters carrying electrodes.

BACKGROUND OF THE INVENTION

Catheter devices having one or more electrodes at their distal end are commonly used for mapping and ablating tissue, e.g., heart tissue. The electrodes are often ring electrodes which are arrayed along a portion of the distal end of the catheter. Most commonly, each of the electrodes is attached to an conductive wire which passes through the inside of the catheter to a controller and power supply outside the catheter. In many cases each of the electrodes is to be individually controlled. As a result, each electrode must be connected to its own conductive wire.

For such devices to be useful the operator must be able to position the electrodes at the precise location to be ablated or mapped. As can be readily imagined, positioning the electrodes at the desired location often involves moving the tip of the catheter along an tortuous path. For example, a catheter can employ a bi-planar deflection system of the type described in U.S. Pat. No. 5,354,297. Such a catheter can be deflected both laterally and vertically. Lateral deflection and control is achieved using a torqueable wire which is more flexible at the distal end than the proximal end. The proximal end of the wire extends out of the catheter and is attached to a rotatable knob. Rotation of this knob transmits rotational torque to the catheter tip. If the distal end of the catheter is deflected vertically, the application of torque causes the tip to deflect laterally. This control system permits precise positioning of the electrodes at a desired location. However, the positioning of the distal end of the catheter, because of the deflection and torquing involved, can place considerable strain on the connection between the electrode and the conducting wire to which it is attached.

Conventionally, ring electrodes are placed on the distal tip of a flexible catheter as follows. A small aperture is made in the wall of the catheter at the location where the electrode is to be positioned, and an insulated conductive wire is threaded distally through the interior of the catheter. The conductive wire is then threaded through the small aperture. The insulation is removed from a distal portion of the conductive wire, and the exposed conductive wire is soldered to the inside of the ring electrode. The ring electrode is then threaded over the distal end of the catheter and slid along the catheter towards the proximal end of the catheter. Simultaneously, the conductive wire is drawn into the catheter through the small aperture until the ring electrode is located over the small aperture and no portion of the conductive wire is visible outside the catheter. This process may strain the connection between the conductive wire and the ring electrode. Assembling a catheter by this process will take a considerable amount of time.

Moreover, if multiple ring electrodes are to be placed on the distal tip of the catheter, the process is considerably more complex and time consuming. For example, if three ring electrodes—a proximal ring electrode, a middle ring electrode, and a distal ring electrode—are to be placed on the distal tip of a catheter, three conductive wires must be passed through the interior of the catheter. The conductive wire for the proximal ring electrode is threaded through a small aperture in the catheter at the ultimate location of the proximal ring electrode, a conductive wire for the middle ring electrode is threaded through a small aperture in the catheter at the ultimate location of the middle ring electrode, and a conductive wire for the distal ring electrode is threaded through a hole at the ultimate location of the distal ring electrode. The conductive wire for the proximal ring electrode is soldered to the proximal ring electrode. The conductive wires for the middle ring electrode and the distal ring electrode are then threaded through the proximal ring electrode, and the conductive wire for the middle ring electrode is soldered to the middle ring electrode. The conductive wire for the distal ring electrode is threaded through the middle ring electrode and soldered to the distal ring electrode. Once all three ring electrodes are attached to their respective conducting wire, the ring electrodes can be passed over the distal end of the catheter and slid towards the proximal end of the catheter while drawing in the excess lengths of conductive wire until each ring electrode is located over the aperture through which its conductive wire passes and each conductive wire is fully within the catheter. In this process the proximal electrode is, of course, placed on the catheter first followed by the middle electrode and finally the distal electrode. As can be easily imagined, the greater the number of electrodes, the more difficult the assembly procedure becomes.

There are other arrangements for attaching a ring electrode to its conducting wire. For example, U.S. Pat. No. 4,444,195 describes a catheter having a number of ring electrodes each of which is attached to a conducting wire. The catheter has multiple pairs of closely spaced apertures—one pair for each ring electrode. Each conductive wire passes through the interior of the catheter until it reaches the pair of openings for its ring electrode. The conductive wire then passes out of the catheter through one aperture of the pair, loops around the catheter, extends over or under the loop and back into the catheter through the other aperture of the pair. A ring electrode is positioned over each pair of apertures and the electrode is bonded by either a compression fit or the use of conductive epoxy interposed between the tubing and the electrode.

SUMMARY OF THE INVENTION

In one aspect, the invention features an electrophysiology catheter which includes:

a catheter tube having a band of electrically conductive ink extending around substantially the entire circumference of the catheter tube; a flexible electrical conductor within the catheter tube, the electrical conductor having a free end extending through an opening in the catheter tube, the free end lying along a portion of the band of electrically conductive ink, the free end being in electrical contact with the band of electrically conductive ink, and an electrically conductive electrode positioned over and in electrical contact with the band of electrically conductive ink and the free end of the conductive wire, the electrode being substantially cylindrical and having a distal end and a proximal end.

In another aspect the invention features a method which includes the following steps:

a) providing a catheter tube;

b) applying a band of electrically conductive material to the outer surface of the catheter tube, the band extending around substantially the entire circumference of the catheter tube;

c) forming an opening through a wall of the catheter tube and the band of electrically conductive material;

d) threading an electrical conductor having a free end through the catheter tube and drawing the free end of the electrical conductor through the said opening;

e) placing the free end of the electrical conductor against the band of conductive material;

f) fitting an electrode over the band of conductive material and the free end of the electrical conductor.

DESCRIPTION OF THE PREFERRED EMBODIMENTS

Figure 1:
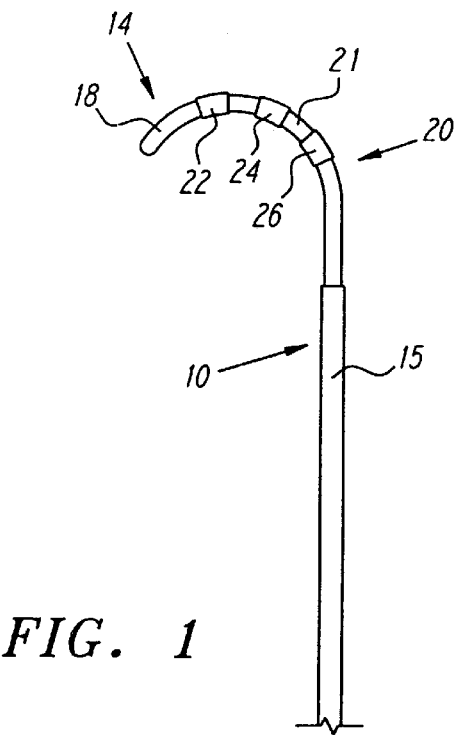
FIG. 1 is a diagrammatic illustration of the distal tip of an electrophysiology catheter.

Referring to FIG. 1, an electrophysiology catheter 10 includes an elongated flexible catheter body 15 and a distal tip portion 14 having a distal terminus 18. The length of the catheter body is typically 48 inches, while the length of the distal tip portion is typically between 1½ and 5 inches. The outer diameter on the catheter body is about between 6 and 7 French, and the outer diameter of the distal tip is about between 5 and 6 French. The choice of catheter dimensions depends on the anatomy of the patient undergoing the procedure and the nature of the procedure. Distal tip portion 14 includes a hollow catheter tube 21 formed from a polyurethane extrusion that is preferably more flexible than the catheter body 15. Three ring electrodes 22, 24, and 26 are shown disposed along the length of the distal tip portion, however, more or fewer electrodes may be disposed. The ring electrodes are preferably compression fitted on catheter tube 21 so that the outer surface of the electrodes forms a more or less continuous surface with the surface of catheter tube 21. For ease of insertion into a body lumen, it is preferred that outer surface of each ring electrode is flush with the outer surface of the catheter tube 21. However, it is also acceptable for the outer surface of each ring electrode to be raised somewhat above the surface of the catheter tube. The ring electrodes are preferably pressure fitted to catheter tube 21. The distal terminus 18 of distal tip portion 14 is rounded to avoid tissue damage (not shown) as catheter is inserted. The distal terminus can include a tip electrode.

Figure 2:
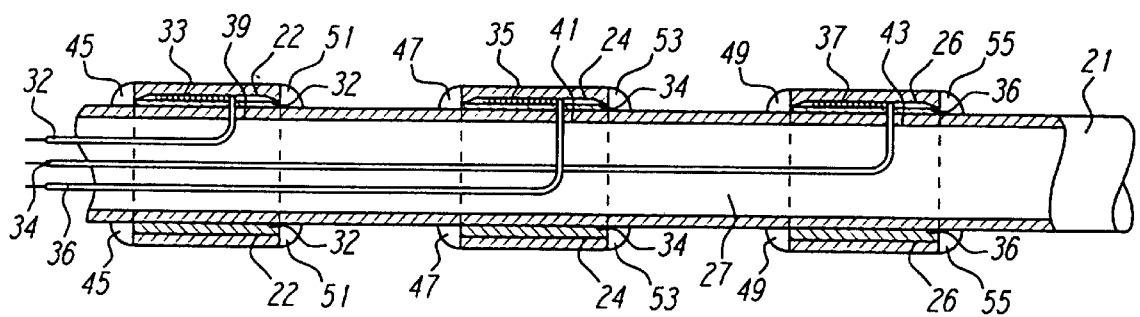
FIG. 2 is a side view, partially cutaway, of a portion of the electrophysiology catheter distal tip of FIG. 1.

As can be seen in FIG. 2, distal tip portion 14 includes a lumen 27 through which pass electrically conductive wires 32, 34, and 36 for supplying current to ring electrodes 22, 24, and 26. Ring electrodes 22, 24, and 26 are positioned over electrically conductive bands 32, 34, and 36 respectively on the outer surface of catheter tube 21. Ring electrodes 22, 24, and 26 are fitted so as to be in electrical contact with electrically conductive bands 32, 34, and 36. The electrically conductive bands are generally printed on the outer surface of the distal tip portion using standard printing methods (e.g., pad printing, spraying, brushing, sputtering, or ion deposition) and electrically conductive ink, e.g., silver-filled ink (e.g., approximately 85% silver, 15% binding material) available from Creative Materials, Taunton, Mass.; (part #114–19). Silver-filled ink has several advantages. Among other advantages, it is resistant to corrosion; it is highly conductive; it adheres well to plastic; and it is easily combined with binder. Because the electrically conductive ink has a relatively low viscosity and does not act as an adhesive, assembly is greatly simplified. The ink can be applied very precisely and allowed to dry completely before the catheter is further assembled. Conductive wires 32, 34, and 36 (e.g., 0.003 double A copper wire) have an insulating coating along substantially their entire length except for distal ends 33, 35, and 37. Distal ends 33, 35, and 37 of conductive wires 32, 34, and 36 pass through openings 39, 41, and 43 in hollow tube 21 and electrically conductive bands 32, 34, and 36 respectively. Distal ends 33, 35, and 37 then extend proximally along the outer surface of conductive bands 32, 34, and 36 respectively beneath ring electrodes 22, 24, and 26 respectively. Ring electrodes 22, 24, and 26 are in electrical contact with distal ends 33, 35, and 37 respectively. Distal ends 33, 35, and 37 can extend distally along the outer surface of conductive bands 32, 34, and 36 or even radially around conductive bands 32, 34, and 36. It is preferred that the distal ends of the conductive wires do not extend beyond the proximal end of the ring electrode with which they are in contact. A small amount of conductive ink can be applied to distal ends 33, 35, and 37 to further improve the electrical connection between the conductive wire and the ring electrode. It is preferred that the portion of the conductive wire actually passing through the wall of the hollow tube be electrically insulated. In addition, it is desirable to secure each conductive wire to hollow catheter tube 21 at opening through which the wire passes using a small amount of adhesive, preferably electrically insulating adhesive. This process secures the conductive wires and provides for strain relief. In addition, an electrically insulating adhesive may be used to secure the ring electrodes to the catheter tube at their proximal 45, 47, and 49 and distal 51, 53, and 55 ends.

Because the non-insulated distal ends of the conducting wires lie on top of an electrically conductive band (created by the electrically conductive ink) which encircles the hollow tube, there is, in effect a 360° electrical connection between each conducting wire and the ring electrode with which it is in contact. This arrangement provides substantial advantages. For example, torquing and bending of distal tip is unlikely to interrupt the entire 360° electrical connection between a conductive wire and its ring electrode. Moreover, the tendency of the conductive wire to sink into the relatively soft material of the catheter tube, particularly when the ring electrode is in place, will not break the electrical connection between the conductive wire and the ring electrode. This is because the conductive wire continues to be in electrical contact with the conductive band even as it is pressed into the hollow tube. Thus, even if the conductive wire is so buried in the hollow tube that it is no longer in physical contact with the ring electrode, it will remain in electrical contact with the ring electrode by virtue of the continuing physical and electrical contact between the conducting wire and the conductive band on the one hand and the ring electrode and the electrically conductive band on the other hand. Accordingly, pressure fitting of the ring electrodes to the catheter tube actually improves the electrical connection between the ring electrode and the conductive wire. This stands in contrast to other arrangements in which pressure fitting can actually impair the electrical connection between the ring electrode and the conductive wire.

The present design reduces the risk of an interruption in the connection between the conductive wire and electrode in other ways. There is no need for hot soldering or welding, both of which can weaken the conductive wire, adding to the risk of breakage or failure. The glue that secures the conductive wire to the catheter tube at the opening through which the wire passes through the wall of the catheter tube provides strain relief. This strain relief protects the distal end of the conductive wire from the strain imparted to the wire as a consequence of moving the catheter tip through the tortuous path which is often followed to properly position the electrodes.

The design of the distal tip of the invention considerably simplifies assembly. The precise order of the various steps can be changed to some extent. The following assembly method is exemplary of how two ring electrodes can be electrically connected to the distal tip of a catheter. First, the electrically conductive bands are printed on the catheter tube using electrically conductive ink. The ink is then allowed to dry completely. Next, the ring electrodes are slid over the distal end of the catheter tube and slid towards the proximal end of the catheter tube until each ring electrode is located just distal to the conductive band over which it is to ultimately be positioned. Third, a small hole is made through the conductive band and hollow tube near the distal end of each conductive band.

Figure 3:
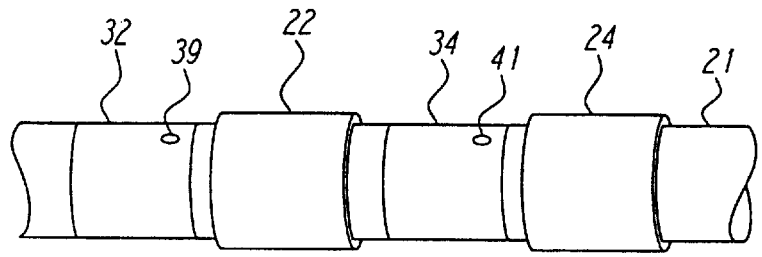
FIGS. 3–5 are diagrammatic illustrations of a portion of partially assembled electrophysiology catheter distal tips.

FIG. 3 illustrates the appearance of a portion of the distal tip after this series of steps. As can be seen, the ring electrode 22 is positioned just distal to conductive band 32 and ring electrode 24 is positioned just distal to conductive band 34. Small openings 39 and 41, sized to permit the insertion of a conductive wire, in both the conductive material and the catheter tube are located toward the distal end of conductive bands 32 and 34.

The conductive wires are threaded into the catheter tube from the proximal end (not shown) and pulled out through the openings in the conductive band and catheter tube. The insulating coating is removed from the portion of each conductive wire extending outside of the catheter tube. A small amount of adhesive, e.g., Loctite 416, is used to secure each conductive wire to the catheter tube and conductive band at the point the conductive wire exits the catheter tube. The conductive wires are trimmed such that when they are extended proximally along the outer surface of the conductive bands they do not extend beyond the proximal ends of the conductive bands.

Figure 4:
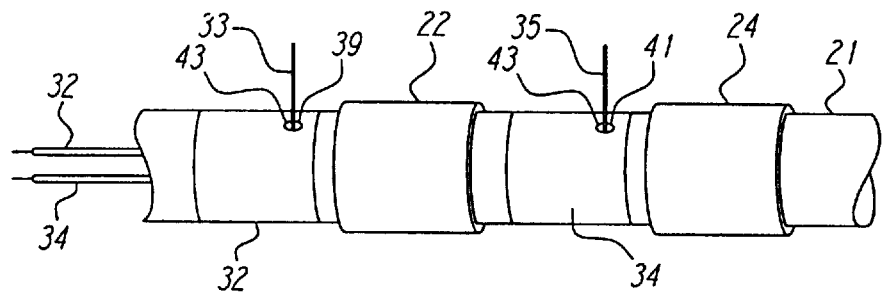

FIG. 4 illustrates the appearance of a portion of the distal tip after this series of steps. As can be seen, conductive wires 33 and 35 extend out of openings 39 and 41 through the conductive band and catheter tube. A small amount of adhesive 43 secures conductive wires 33 and 35 to catheter tube 21 at the opening through which they pass.

Next, the conductive wires are folded down to run along the outer surface of the conductive bands in a proximal direction. At this point the conductive wire, and any portions of the conductive band which may have become worn, can be coated with additional conductive ink.

Figure 5:
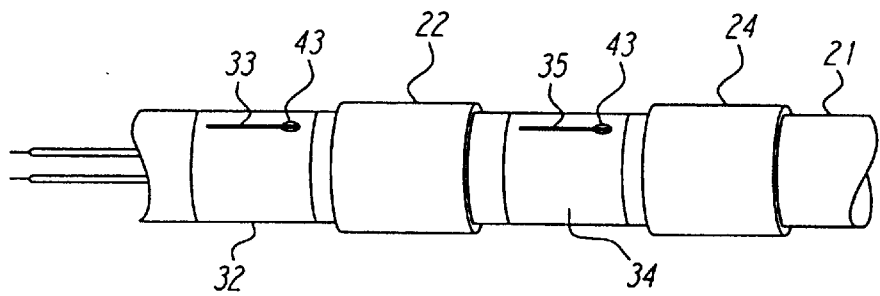

FIG. 5 illustrates the appearance of a portion of the distal tip after this series of steps. As can be seen, conductive wires 33 and 35 extend along the outer surface of conductive bands 32 and 34 in the proximal direction. Next, the ring electrodes are slid towards the proximal end of the distal tip region, as indicated by the arrow in FIG. 5, until each ring electrode is positioned over the conductive band to which is out of openings through the conductive band and catheter tube. A small amount of a non-conductive adhesive 45 and 47 can be applied around the proximal ends of ring electrodes 22 and 24 to secure them to the catheter tube. A small amount of a non-conductive adhesive 51 and 53 can be place around the distal ends of electrodes 22 and 24 for the same purpose.

Figure 6:
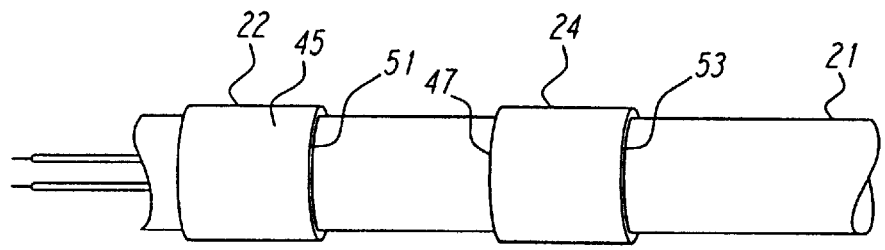
FIG. 6 is a diagrammatic illustration of a portion of an assembled electrophysiology catheter distal tip.

FIG. 6 illustrates the appearance of a portion of the distal tip after this series of steps. As can be seen in this figure, both ring electrode 22 and ring electrode 24 completely cover the conductive band and conductive wire with which their are in contact. A small amount of a non-conductive adhesive 45 and 47 is present around the proximal ends of ring electrodes 22 and 24 to secure them to the catheter tube.

A small amount of a non-conductive adhesive 51 and 53 is present around the distal ends of electrodes 22 and 24 for the same purpose.

The electrodes of the present catheter can be used in conventional methods for sensing, pacing, or ablation. The methods described above can also be used to prepared catheters carrying electrodes of other types, e.g., temperature sensing electrodes.

What is claimed is:

1. An electrophysiology catheter comprising:
    a catheter tube having a band of electrically conductive ink extending around substantially the entire circumference of said catheter tube;
    a flexible electrical conductor within said catheter tube, said electrical conductor having a free end extending through an opening in said catheter tube, said free end lying along a portion of said band of electrically conductive ink, said free end being in electrical contact with said band of electrically conductive ink; and
    an electrically conductive electrode positioned over and in electrical contact with said band of electrically conductive ink and said free end of said conductive wire, said electrode being substantially cylindrical and having a distal end and a proximal end.

2. The electrophysiology catheter of claim 1 wherein a portion of said conductive wire that is not lying along said band of electrically conductive ink is coated with an insulating material.

3. The electrophysiology catheter of claim 1 wherein said opening in said catheter tube is within said non-adhesive electrically conductive band.

4. The electrophysiology catheter of claim 1 wherein said band of electrically conductive ink has a substantially uniform width.

5. The electrophysiology catheter of claim 1 wherein said free end of said conductive wire has a length which does not extend beyond either the distal end or the proximal end of said electrode.

6. The electrophysiology catheter of claim 1 wherein said band of electrically conductive ink has a length which does not extend beyond either the distal end or the proximal end of said electrode.

7. The electrophysiology catheter of claim 1 further comprising an adhesive to secure said electrical conductor to said catheter tube where said electrical conductor passes through said opening in said catheter tube.

8. The electrophysiology catheter of claim 1 wherein said portion of electrical conductor lying along said band of electrically conductive ink is coated with an electrically conductive material.

9. The electrophysiology catheter of claim 1 wherein said electrically conductive ink comprises silver-filled ink.

10. A method comprising:
    (a) providing a catheter tube;
    (b) applying a band of electrically conductive material to the outer surface of said catheter tube, said band extending around substantially the entire circumference of said catheter tube;
    (c) forming an opening through a wall of said catheter tube and said band of electrically conductive material;
    (d) threading an electrical conductor having a free end through said catheter tube and drawing said free end of said electrical conductor through said opening;
    (e) placing said free end of said electrical conductor against said band of conductive material;
    (f) fitting a substantially cylindrical electrode over said band of conductive material and said free end of said electrical conductor.

* * * * *